United States Patent [19]

Takeba

[11] Patent Number: 5,189,145
[45] Date of Patent: Feb. 23, 1993

[54] FLOWER-INDUCING SUBSTANCES AND A METHOD FOR PRODUCTION THEREOF

[75] Inventor: Go Takeba, No. 6–18, Kitaoji 3-chome, Otsu-shi, Shiga-ken, Japan

[73] Assignees: Ajinomoto Co., Inc., Tokyo; Go Takeba, Otsu, both of Japan

[21] Appl. No.: 584,620

[22] Filed: Sep. 19, 1990

[30] Foreign Application Priority Data

Sep. 21, 1989 [JP] Japan .................. 1-243387
Mar. 23, 1990 [JP] Japan .................. 2-71973
May 10, 1990 [JP] Japan .................. 2-118712
Jun. 21, 1990 [JP] Japan .................. 2-163716

[51] Int. Cl.⁵ .............................. C07K 1/00
[52] U.S. Cl. .......................... 530/326; 504/287; 504/117
[58] Field of Search ............. 530/326; 71/106

[56] References Cited

U.S. PATENT DOCUMENTS 4,818,274 4/1989 Bridle et al. .................. 71/106

OTHER PUBLICATIONS

Chemical Abstracts, vol. 110, 1989, p. 423, abstract No. 92177d, Columbus, Ohio, US; M. Ono et al.: "In vitro translated polypeptides of different organs of *Pharbitis nil chois.*, strain Violet under flower-inductive and non-inductive conditions", & Plant Sci., (Limericj, Irel.), 1988, 58(1), 1–7 *Abstract*.
Plant Physiol, (1974), 54, pp. 904–906, "Identification of the Flower-Inducing Factor Isolated from Aphid Honeydew . . . ", Cleland.

Primary Examiner—John W. Rollins
Attorney, Agent, or Firm—Oblon, Spivak, McClelland, Maier & Neustadt

[57] ABSTRACT

Flower-inducing substances containing protein or peptide materials and obtained by extraction of plant materials with water.

8 Claims, 4 Drawing Sheets

FLOWER-INDUCING SUBSTANCES AND A METHOD FOR PRODUCTION THEREOF

BACKGROUND OF THE INVENTION

The process in agriculture of cultivating plants and causing them to bloom and/or bear fruit directly affects the yield and is important for determining economical value. In crops, fruits, vegetables and decorative flowering plants, products are formed after flowering so that the flowering period determines the period for yielding and/or shipment. Accordingly, a technique for regulating the flowering of plants in an inexpensive way makes a planned agricultural production possible and brings about an innovation in agriculture. The present invention is directed to flower-inducing substances for carrying out the foregoing concept which can be widely utilized in general and to methods for producing the flower-inducing substances.

In many cases, plants change their mode of growth from vegetative growth to reproductive growth, depending upon daily periodicity, and form flower buds on meristematic tissue and finally bloom. A group of plants which flower when daytime becomes long and nighttime becomes short are called long-day plants and a group of plants which bloom when daytime becomes short and nighttime becomes long are called short-day plants. Cabbage and spinach are long-day plants and chrysanthemum, morning glory, strawberry, rice plants, wheat, etc. are short-day plants. In addition, there are plants which induce flower buds in response to temperature. Dendrobium, which is one species of orchid, is a typical plant which induces flower buds at a low temperature. In order to induce flower buds on cabbage or spinach, a low temperature is required, in addition to long days.

As stated above, plants form flowers and bloom depending upon environmental conditions inherent to their species. However, it is considered that a substance for inducing the reaction of forming flower buds would be common to any plants. Where plants are put under environmental conditions which are inherent to the respective plants but in which flowering is induced, a common substance is synthesized, acts on the meristematic tissue and induces flower buds there.

DESCRIPTION OF THE PRIOR ART

Fifty years ago, Chailakhyan predicted the presence of a flowering hormone which would be synthesized in leaves and transported through the fluid in sieve tubes. Subsequent grafting experiments revealed that the flowering hormone is present in many species of plants and has a wide spectrum of activity. For example, the experimental fact that by grafting a non-flower-induced sweet potato on a flower-induced morning glory, the sweet potato opens its flowers, indicates that the flowering hormone for morning glory is also effective for sweet potato.

The first report on the isolation and determination of a substance having flower-inducing activity was made by Cleland et al. (C. F. Cleland and A. Ajami, Plant Physiol., 54, 904). Cleland et al. isolated a substance assumed to have a flower-inducing activity from honeydew of plant lice containing the sieve tube fluid of burweed, which is a short-day plant, using as an index flower induction of *Lemna gibba*, and clarified that the substance was salicylic acid. However, when salicylic acid was given to burweed, no flower induction was caused. However, this experimental result was very influential and many research groups assumed that the entity of the flowering hormone would be a lower molecular phenolic substance such as salicylic acid and attempted to isolate the flower-inducing substance from the extract of leaves with methanol or with acetone. As a result, benzoic acid, nicotinic acid, nicotinamide, pipecolic acid, etc. were found in *Lemma gibba* or analogous plants, as flower-inducing substances. These substances cannot induce flowering in other higher plants. In addition, since these substances are present within the body of plants, irrespective of flower-induction, they are not considered to be flowering hormones.

SUMMARY OF THE INVENTION

An object of the present invention is to isolate a naturally-occurring flowering hormone usable as a plant growth regulator in order to control the flowering of plants in an inexpensive way.

The flower-inducing substance as used in the present invention is not particularly limited as long as it is a substance having flower-inducing activity.

The kind of plants from which the flower-inducing substance is extracted is not particularly limited but plants belonging to the families Lemnaceae, Convolvulaceae, etc., are preferred. The family Lemnaceae covers the genus Lemna, the genus Spirodela, the genus Wolffia, the genus Wolffiella, etc., and plants belonging to any genus may be used but *Lemna paucicostata* and *Lemna gibba* are preferred. As plants belonging to the family Convolvulaceae, for example, *Pharbitis nil chois* is preferred. Plants extracted are preferably flower-induced plants.

It is considered that the flower-inducing substance would be synthesized in leaves and transported to the whole body of plant via sieve tube fluid. Therefore, the flower-inducing substance can be extracted from any part of plants but leaves are particularly preferred as extraction sites.

The flower-inducing substance can be obtained by grinding the plants into pieces and extracting with water. The method of grinding may be carried out in such a manner that the epidermis is destroyed and the inside of plants can be extracted with water. For example, plants are cut into pieces with a cutter. Extraction with water may be performed by putting the plant pieces in water followed by stirring, if necessary. For the extraction, phosphate buffer, etc. may also be utilized, in addition to water. The pH value of the buffer is preferably from about 5 to about 8. The time period for the extraction may be approximately one to 60 minutes at normal temperature. For enhancing the speed of extraction, heating may also be performed. After extraction with water, insoluble matter is removed by means of centrifugation, filtration, etc., if necessary, followed by purification. For the purification, known means such as fractionation of peptides by their molecular weight can be used. Furthermore, for example, gel filtration, ion exchange chromatography, precipitation with ammonium sulfate, etc. may also be utilized.

For assaying the flower-inducing activity, any plant may be used but plants belonging to the family Lemnaceae are preferable. The plants belonging to the family Lemnaceae have a small body and a rapid proliferation rate and rapidly absorb organic matter such as sugar, etc. In addition, many kinds of varieties which have different conditions for flower induction are present and, after flower induction, the time period until differentiation of flowers is short. Therefore, these plants have excellent properties for assaying the flower-inducing substance. Any plant is usable so long as it belongs to the family Lemnaceae but for example, Lemna paucicostata and Lemna gibba are preferred. On the other hand, when the flower-inducing activity is assayed in higher plants other than the family Lemnaceae, for example, Pharbitis nil chois may be used. Pharbitis nil chois is a plant showing strong short-day characteristics so that it can be sensitive to daytime immediately after the evolution and greening of cotyledon. The kind of Pharbitis nil chois is not particularly limited but the Violet variety may be used as a species having a particularly strong short-day property.

For assaying the flower-inducing activity in plants belonging to the family Convolvulaceae, the following method is used. That is, 3 fronds of thalli are cultured in 25° C. in an Erlenmeyer flask of 30 ml volume charged with 10 ml of 1/10M medium for Lemna gibba under continuous lighting. A variety of substances are added to the medium and one week after, differentiated flower buds are observed by a stereoscopic microscope. Thus, the effect of the added substance on flower induction is evaluated.

Further, for assaying the flower-inducing activity in Pharbitis nil chois, there may be used methods in which a sample substance is given to the stub upon sprinkling to absorb it through the root; a sample substance is sprayed over leaves; a defatted cotton thread is passed through the stalk or hypocotyl and the tip of the thread is dipped in water containing a sample substance to directly absorb the sample into vascula bundles, etc.

The flower-inducing substance of the present invention includes 4 types having molecular weights of 80 to 150 kilodaltons, 20 to 30 kilodaltons, 3 to 10 kilodaltons and 0.6 to 1.2 kilodaltons, respectively, when measured by the gel filtration method. Among them, the substances having molecular weights of 80 to 150 kilodaltons, 20 to 30 kilodaltons and 3 to 10 kilodaltons are present in plants irrespective of flower induction. The substances having molecular weights of 0.6 to 1.2 kilodaltons appear remarkably upon flower induction, but they may be decomposition products of the flower-inducing substance having a molecular weight of 80 to 150 kilodaltons, 20 to 30 kilodaltons or 3 to 10 kilodaltons.

Further, the substances having molecular weights of 20 to 30 kilodaltons may be decomposition products of the substances having molecular weights of 80 to 150 kilodaltons, and the substances of 3 to 10 kilodaltons may be decomposition products of the substances of 80 to 150 kilodaltons or 20 to 30 kilodaltons. The molecular weights described above vary somewhat, depending upon methods for measurement, etc.

It is considered that these flower-inducing substances are proteinaceous substances since they are inactivated by treatment with aminopeptidase M. Furthermore, the flower-inducing activity of these substances is not lost even after treatment with chymotrypsin.

The flower-inducing substances contain the following amino acid sequence in the molecule thereof as a part of their structures:

Ser-Gln-Leu-Pro-Leu-Val-Gly-Asn-Thr-Ala-Pro-Asn-Phe-Glu-Ala-Glu-Ala-Val-Phe-Asp-Gln

The purified standard substances are also expected to induce flowering in crops, fruits, vegetables, decorative flowering plants and Pharbitis nil chois when these are assayed.

The flower-inducing substances of the present invention are present also in decomposition products with protease such as trypsin, arginyl endopeptidase, etc., in addition to chymotrypsin. For example, the flower-inducing activity is noted in several kinds of peptide obtained by enzymolysis with arginyl endopeptidase, as shown in the following examples.

EXAMPLE 1

Purification of flower-inducing substance in the extract of leaves of short-day Lemna paucicostata 441 with water Thallus of Lemna paucicostata 441 cultured under short-day conditions (namely, flower-induced) was frozen with liquid nitrogen and ground into pieces. The pieces were suspended in 1 ml of 10 mM potassium-phosphate buffer (pH 6.2) per 1 g of thallus. Insoluble matters were removed by centrifugation to give the aqueous extract. The flower-inducing activity of the aqueous extract was assayed using flower induction in Lemna paucicostata 151 as an index. The substance to be assayed for its flower-inducing activity was added to 1/10M medium having the composition shown in Table 1 in various concentrations and 3 fronds of thalli from Lemna paucicostata 151 were inoculated on the medium followed by culture at 25° C. under continuous lighting. One week later, differentiated flower buds were observed with a stereoscopic microscope. The flower-inducing activity is expressed in terms of FL (%) which is shown by percentage of the number of buds per 1 frond. The results of the assay are shown in FIG. 1, wherein the coordinate indicates FL (%) and the abscissa indicates the volume of the extract (ml/g.frond). The results reveal that the aqueous extract contained the flower-inducing activity indicating dose-response as shown in the figure.

TABLE 1

| Composition of Medium M | |
|---|---|
| Ca(NO$_3$)$_2$.4H$_2$O | 5.0 mM |
| MgSO$_4$.4H$_2$O | 2.0 mM |
| KNO$_3$ | 15.0 mM |
| KH$_2$PO$_4$ | 5.0 mM |
| FeCl$_3$.6H$_2$O | 0.02 mM |
| Tartaric acid | 0.02 mM |
| H$_3$BO$_3$ | 0.046 mM |
| MnCl$_2$.4H$_2$O | 0.018 mM |
| ZnSO$_4$.7H$_2$O | 0.00077 mM |
| Na$_2$MoO$_4$.2H$_2$O | 0.0005 mM |
| CuSO$_4$.5H$_2$O | 0.00033 mM |
| | (pH 4.2) |

Next, in order to examine the distribution of the flower-inducing activity by molecular weight, 10 ml of the aqueous extract was passed through a column of $\phi$ 2.6 × 68 cm packed with Sephacryl S-200HR (manufactured by Pharmacia) at a flow rate of 0.5 ml/min. The eluting agent was 10 mM of potassium phosphate buffer (pH 6.2). The obtained elution curve is shown in FIG. 2, wherein the ordinate indicates FL (%) and the abscissa indicates the elution volume. The molecular weights of peak A, peak B and peak C correspond to 80 to 150 kilodaltons, 20 to 30 kilodaltons and 3 to 10 kilodaltons, respectively.

Next, 10 ml. of the extract of leaves from Lemna paucicostata 441 cultured under short-day conditions (namely, flower-induced) and 10 ml of the aqueous extract of leaves from *Lemna paucicostata* 441 cultured under continuous lighting (namely, not flower-induced) were passed through a column of $\phi$ 2.6×65 cm packed with Bio Gel P-6 (manufactured by Bio-Rad Co., Ltd.) at a flow rate of 0.5 ml/min, respectively. The eluting agent was 10 mM potassium-phosphate buffer (pH 6.2). The obtained elution curves are shown in FIG. 3, wherein the ordinate indicates FL (%) and the abscissa indicates an elution volume. The solid line and the broken line indicate the case cultured under continuous lighting and the case cultured under short-day conditions, respectively. The column has a high dissolving power in the low molecular side. In the case of culturing under short-day conditions, a new peak (D) of 0.6 to 1.2 kilodaltons appears in addition to the previous 3 activity peaks. This indicates that the peak of 0.6 to 1.2 kilodaltons is a substance having flower-inducing activity corresponding to the flower-inducing conditions.

After the purified standard of Fraction B obtained above and shown in FIG. 2 was treated with protease K, it was treated with 20 U/ml of aminopeptidase M or 20 U/ml of chymotrypsin in 10 mM potassium-phosphate buffer (pH 6.2), respectively, and the flower-inducing activity to *Lemna paucicostata* 151 was assayed.

The results are shown in Table 2.

TABLE 2

| Results of Protease Sensitivity Test | | |
|---|---|---|
| | | FL |
| Aminopeptidase M | not treated | 60.2% |
| | treated | 0.0% |
| Chymotrypsin | not treated | 62.4% |
| | treated | 59.8% |

As stated above, in each fraction, the activity was markedly reduced by aminopeptidase M but no reduction was noted by treatment with chymotrypsin. With respect to the other fractions having the flower-inducing activity shown in FIGS. 2 and 3, similar tests were performed so that similar results were obtained. From the foregoing results, it is shown that the active substance is a proteinaceous substance.

The solution containing the fraction of 0.6 kilodaltons to 1.2 kilodaltons in the aqueous extract of *Lemna paucicostata* was directly given to *Pharbitis nil chois* (species, "Violet") through a cotton thread passed through the hypocotyl of *Pharbitis nil chois*, whereby positive or negative flower induction in *Pharbitis nil chois* was examined. After administration, short-day was given once followed by cultivation under continuous lighting. One week later, the number of differentiated buds was counted (in general, flower is not induced under these conditions).

The results are shown in Table 3.

TABLE 3

| Flower-Inducing Activity in the 0.6 KD-1.2 KD Fraction to Morning glory | | |
|---|---|---|
| Number of Specimen | Number of Flower Inductions | Blooming Rate (%) |
| Not treated 20 | 0 | 0 |
| Treated 20 | 20 | 100 |

The flower-inducing substance of 0.6 to 1.2 kilodaltons is expected to have flower-inducing activity also in *Pharbitis nil chois*, crops, fruits, vegetables and decorative flowering plants.

EXAMPLE 2

Purification of flower-inducing substance in the aqueous extract of cotyledon of *Pharbitis nil chois*

*Pharbitis nil chois*, species "Violet", was subjected to short-day treatment immediately after evolution and greening of the cotyledon. After the thus treated cotyledon was frozen with liquid nitrogen and ground into pieces, the pieces were suspended in 1 ml of 10 mM potassium-phosphate buffer (pH 6.2) per 1 g of the cotyledon. The suspension was treated as in the case of *Lemna paucicostata* to give the aqueous extract. With regard to the aqueous extract, its flower-inducing activity and molecular weight distribution were determined in a manner similar to Example 1. Almost the same results shown in FIGS. 1 and 2 were obtained. From the results, it is shown that the flower-inducing activity in the aqueous extract of *Pharbitis nil chois* has the molecular weight distribution as in *Lemna paucicostata*.

EXAMPLE 3

Purification of the fraction corresponding to 80 to 150 kilodaltons by gel filtration among the flower-inducing substances in the aqueous extract of thallus of short-day *Lemna paucicostata* 441

Purification was performed using the aqueous extract from *Lemna paucicostata* 441 prepared by the method described in Example 1, while confirming its flower-inducing activity by the assay method shown in Example 1. Firstly, the aqueous extract was subjected to salting-out with ammonium sulfate and the fraction precipitated with 40% saturation was recovered. The precipitates were dissolved in 10 mM potassium-phosphate buffer (pH 6.2) and dialyzed to the same buffer 3 times. After the dialysis, the dialysate was subjected to gel filtration using Bio Gel A 1.5 m $\phi$ 2.6×65 cm (manufactured by Bio-Rad Co., Ltd.). The active fraction showing a molecular weight of 80 to 150 kilodaltons was collected. Next, ion exchange chromatography using MonoQ HR5/10 (manufactured by Pharmacia) was carried out. As buffer, 20 mM piperazine buffer (pH 6.0) was used and elution was performed by linear gradient (0→1M) of NaCl aqueous solution. The active fraction was eluted at about 0.5M of the NaCl aqueous solution. This active fraction was further subjected to reverse phase chromatography using ProRPC HR5/10 (manufactured by Pharmacia). As the moving phase, A and B shown below were used and elution was carried out by linear gradient of A 100%→B 100% during 0 to 120 minutes.

(A: aqueous solution containing 0.1% trifluoroacetic acid

B: acetonitrile solution containing 0.1% trifluoroacetic acid

The active fraction was further purified by SDS polyamide gel electrophoresis. As the result, the active fraction was separated into 2 bands having molecular weights of about 53,000 and about 61,000. In both, the flower-inducing activity was noted, but stronger flower-inducing activity was recognized in the fraction having a molecular weight of about 53,000.

EXAMPLE 4

Decomposition of the flower-inducing substance by peptidase and purification of the decomposition product having activity The aqueous extract of thallus from short-day *Lemna paucicostata* 441 was purified by the same procedure as in Example 3 to give the purified standard of the flower-inducing substance. However, ion exchange chromatography was carried out with MonoQ HR 10/10 (manufactured by Pharmacia) with the buffer (pH 8.5) and reverse phase chromatography was carried out with RepRPC HR 5/5 (manufactured by Pharmacia). The time period required for the purification was about twice that of Example 3. The sample containing the desired product during the course of purification was stored as in Example 3 and allowed to stand at a temperature as low as 4° C.

With respect to the purified standard substance, its molecular weight was confirmed by SDS polyacrylamide gel and a strong flower-inducing activity was noted at about 21 kilodaltons.

A part of the purified standard substance obtained above was treated with 0.5 U/ml of arginyl endopeptidase in 50 mM Tris-hydrochloride buffer (pH 8.5) at 37° C. for 6 hours. After the reaction solution was boiled, the centrifugal supernatant was subjected to reverse phase chromatography using PepRPC HR5/5. Conditions for elution were as follows:

Elution speed: 1 ml/min (23±2° C.)
Eluting solution A: aqueous solution containing 0.1% trifluoroacetic acid
B: acetonitrile solution containing 0.1% trifluoroacetic acid (eluted by linear gradient of A 100%→B 100% from 0 minute to 120 minutes and, 120 minutes after, by B 100%)
Wavelength measured: absorbance at wavelength of 210 mn.

The aforesaid reverse phase chromatogram is shown in FIG. 4. In FIG. 4, the coordinate shows absorbance and the abscissa shows time.

The flower-inducing activity of the fractions shown by numerals in the figure including the peaks to Lemna paucicostata 151 was assayed. The results are shown in Table 4.

TABLE 4

| Flower-inducing Activity of Flower-inducing Substances to the Peptidase Decomposition Products | |
|---|---|
| Peak Number | Rate of Fronds with Buds to Total Fronds, FL (%) |
| 1 | 60 |
| 2 | 90 |
| 3 | 80 |
| 4 | 35 |
| 5 | 50 |

The above results reveal that some of the decomposition products of the flower-inducing substance by arginyl endopeptidase, etc. had the flower-inducing activity.

EXAMPLE 5

Analysis of amino acid sequences in flower-inducing substances

The purified standard substance having a molecular weight of about 21 kilodaltons which was purified in Example 4 and was recognized to have a flower-inducing activity was subjected to high performance liquid chromatography again using ODS Column (Senshu pak. Vp-318-1251).

Conditions for elution were as follows:
Elution speed: 1 ml/min (23 2° C.)
Eluting solution A: 20% acetonitrile solution containing 0.1% trifluoroacetic acid
B: acetonitrile solution containing 0.08% trifluoroacetic acid (eluted by linear gradient of A 100% B 100% from 0 minute to 40 minutes and, 40 minutes after, by B)
Measurement: absorbance at wavelength of 220 nm.

The aforesaid reverse phase chromatogram is shown in FIG. 5. In FIG. 5, the coordinate shows absorbance and the abscissa shows time.

After freeze-drying the fraction shown by A in the figure, it was dissolved in 5% trifluoroacetic acid solution and the solution was subjected to gaseous phase analysis using a 470A Protein Sequencer (Applied Biosystems). The purity of the protein in the fraction A was more than about 95% by SDS-polyacrylamide gel electrophoresis.

The obtained amino acid sequence was:

Ser-Gln-Leu-Pro-Leu-Val-Gly-Asn-Thr-Ala-Pro-
Asn-Phe-Glu-Ala-Glu-Ala-Val-Phe-Asp-Gln.

From this fact, it is revealed that the substance having flower-inducing activity is a protein having at least a part of the amino acid sequence described above or the decomposition products of the protein.

According to the present invention, a means for regulating blooming of various general plants can be provided at low costs.

I claim:

1. A protein or peptide composition having a flower-inducing activity and comprising the following amino acid sequence in its molecule:

Ser-Gln-Leu-Pro-Leu-Val-Gly-Asn-Thr-Ala-Pro-
Asn-Phe-Glu-Ala-Glu-Ala-Val-Phe-Asp-Gln and being substantially free of plant materials insoluble in water.

2. A purified flower-inducing composition comprising a protein or peptide containing the following amino acid sequence in its molecule:

Ser-Gln-Leu-Pro-Leu-Val-Gly-Asn-Thr-Ala-Pro-
Asn-Phe-Glu-Ala-Glu-Ala-Val-Phe-Asp-Gln and having a molecular weight range selected from the group consisting of 80 to 150 kilodaltons, 20 to 30 kilodaltons, 3 to 10 kilodaltons, and 0.6 to 1.2 kilodaltons, when measured by the gel filtration method, whose flower-inducing activity is not inactivated by treatment with chymotrypsin or arginyl endopeptidase, but is inactivated by treatment with aminopeptidase M, and which is produced by extracting plants with water and purifying the extracted material.

Figure 1:
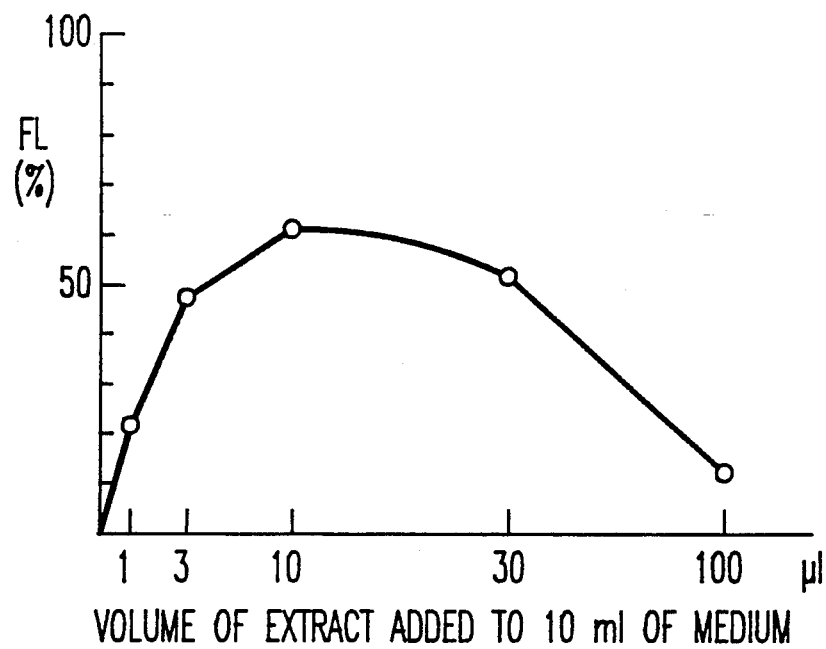
FIG. 1 is a graph showing the relationship between concentration and aqueous extract of the aqueous extract of thallus of Lemna paucicostata.
Figure 2:
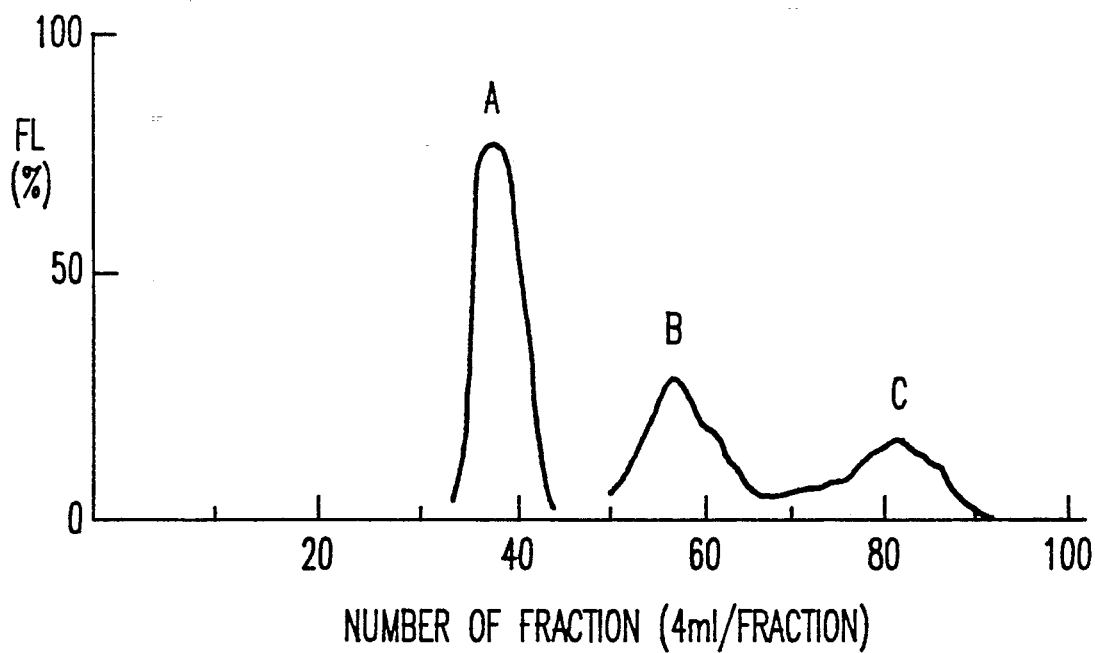
FIGS. 2 and 3 indicate graphs showing changes in the flower-inducing activity of the fraction eluted by passing the aqueous extract through a gel filtration column.
Figure 3:
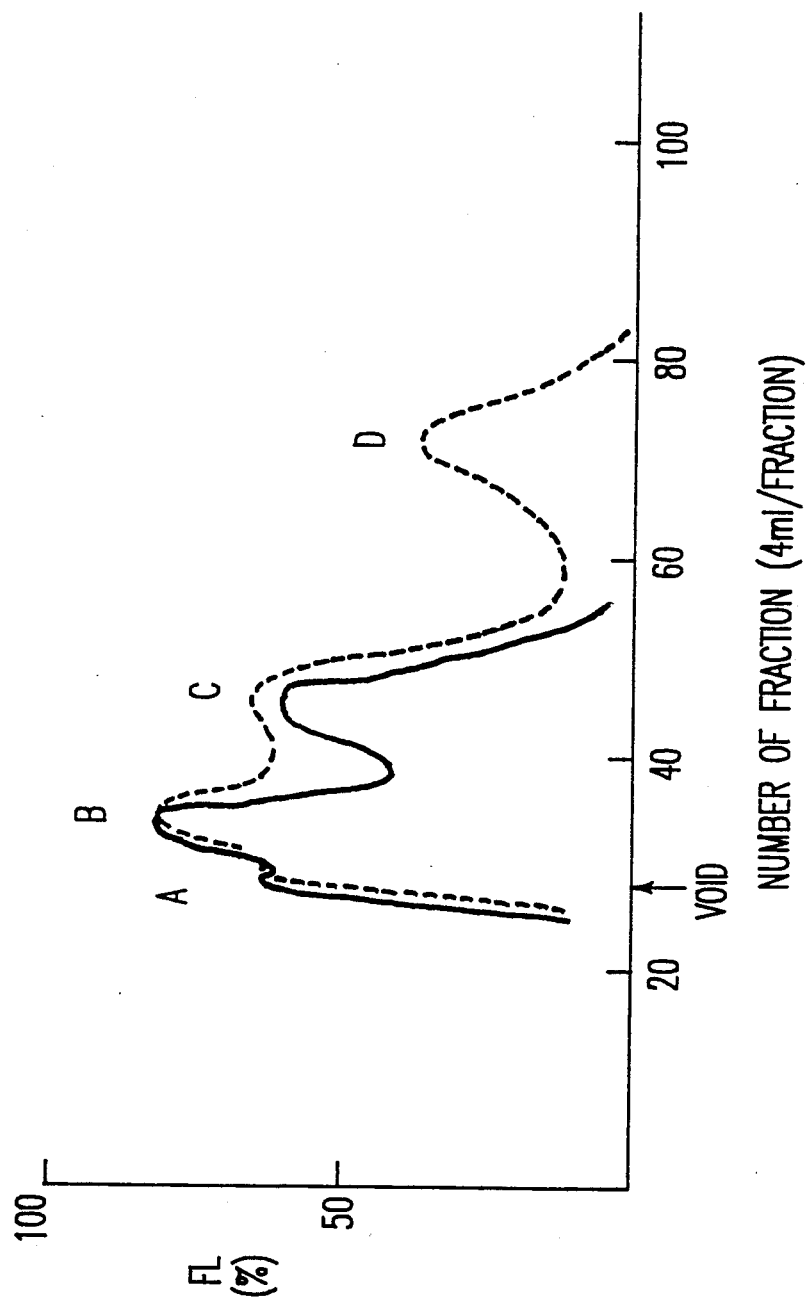
Figure 4:
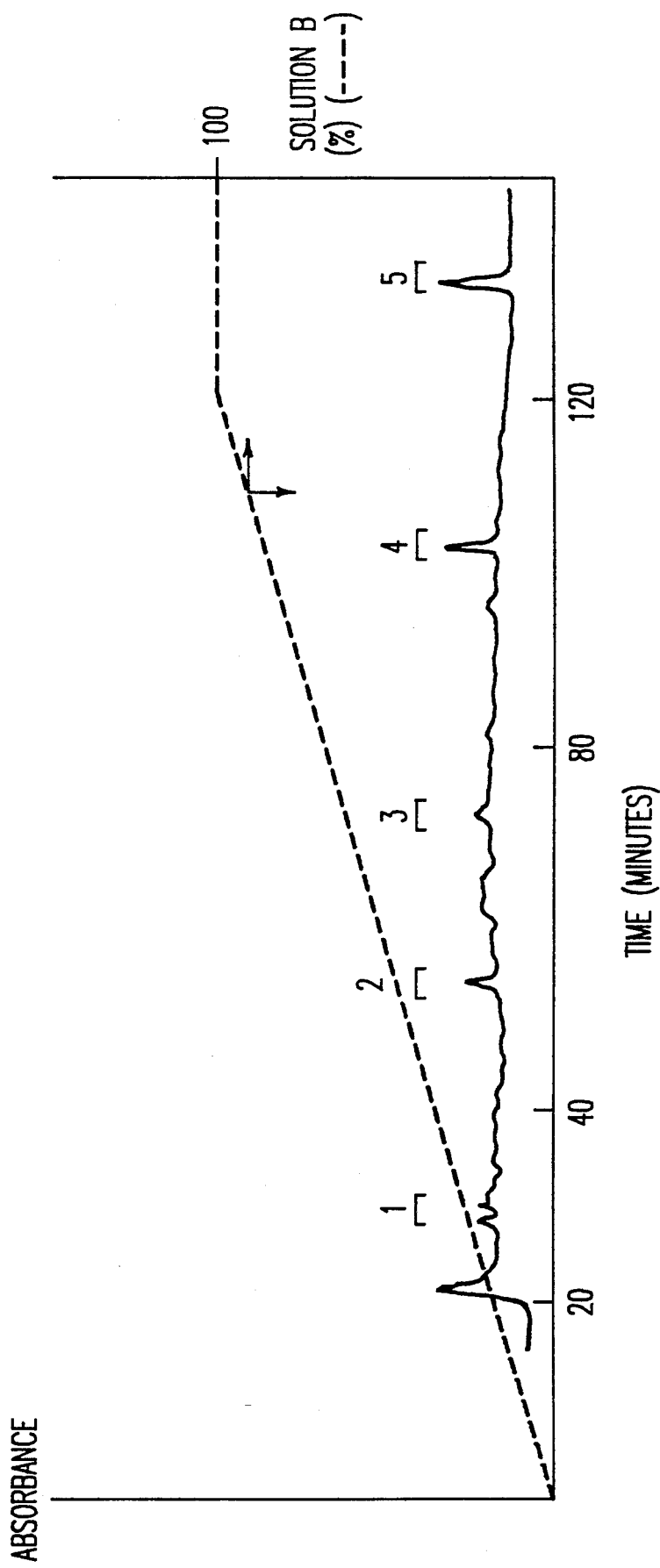
FIG. 4 shows a reverse phase chromatogram of the flower-inducing substance treated by arginyl endopeptidase which had a molecular weight of about 21 kilodaltons.
Figure 5:
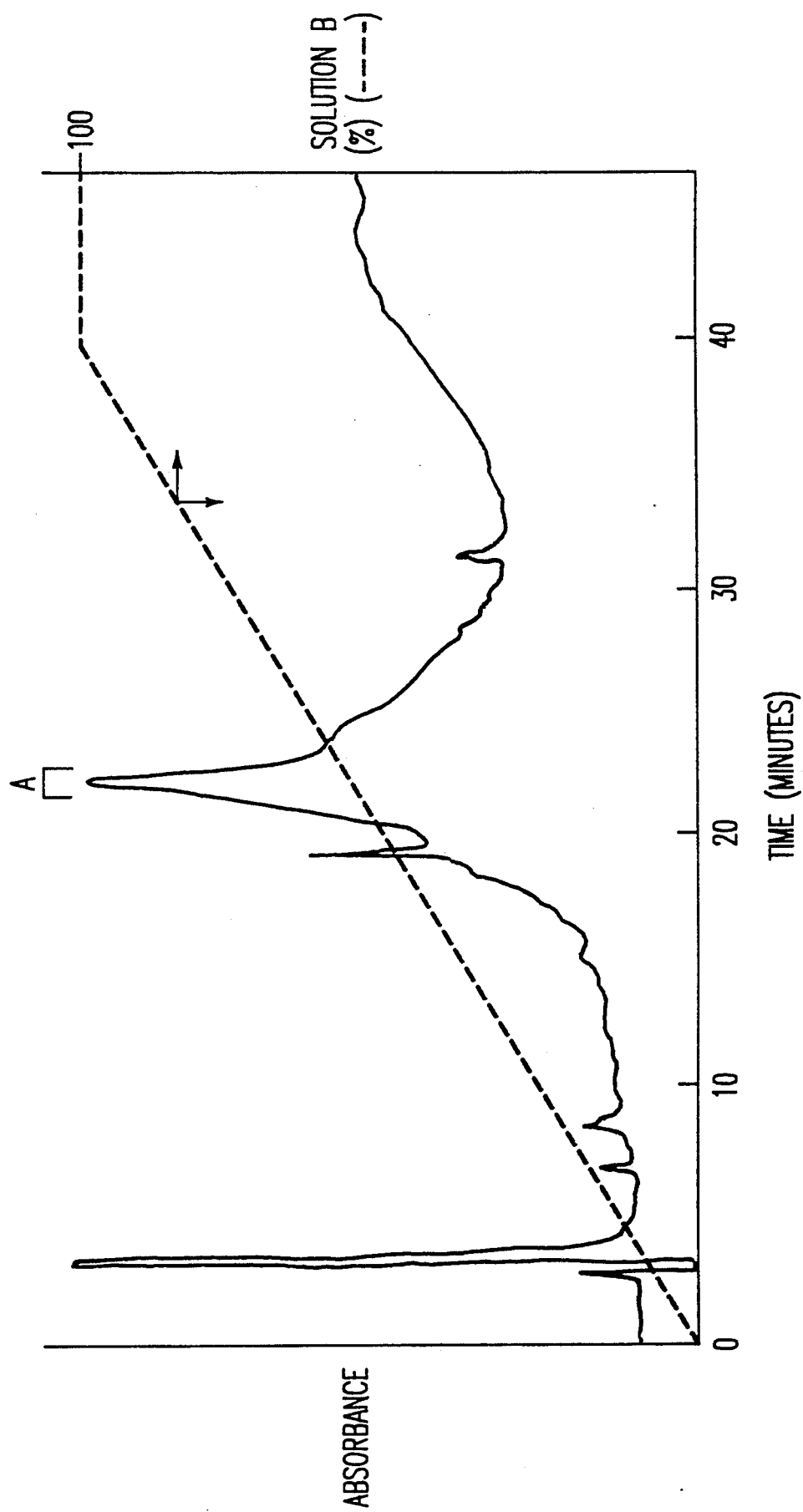
FIG. 5 shows a reverse phase chromatogram of the flower-inducing substance sample having a molecular weight of about 21 kilodaltons.

3. A flower-inducing composition according to claim 2, comprising as a constituent component at least one of the peptides designated by peaks 1, 2, 3, 4 and 5 in FIG. 4.

4. A flower-inducing composition according to claim 1, which is produced by the process comprising extracting leaves of *Lemna paucicostata* with water, centrifuging, and separating the aqueous extract from insoluble materials, and containing peptide materials having molecular weights of 80 to 150 kilodaltons, 20 to 30 kilodaltons, and 3 to 10 kilodaltons.

5. A flower-inducing composition according to claim 4, additionally comprising protein or peptide material having a molecular weight of 0.6 to 1.2 kilodaltons.

6. A flower-inducing composition according to claim 1, obtained by the process comprising extracting cotyledon of *Pharbitis nil chois* with water.

7. A flower-inducing composition according to claim 1, comprising active fractions having molecular weights of about 53,000 and about 61,000.

8. A purified flower-inducing composition according to claim 1 consisting essentially of a protein or peptide having a molecular weight of about 21 kilodaltons and containing the amino acid sequence:

Ser-Gln-Leu-Pro-Leu-Val-Gly-Asn-Thr-Ala-Pro-Asn-Phe-Glu-Ala-Glu-Ala-Val-Phe-Asp-Gln.

* * * * *

UNITED STATES PATENT AND TRADEMARK OFFICE
CERTIFICATE OF CORRECTION

PATENT NO. : 5,189,145
DATED : FEBRUARY 23, 1993
INVENTOR(S) : GO TAKEBA

It is certified that error appears in the above-indentified patent and that said Letters Patent is hereby corrected as shown below:

Column 4, line 43, "MgSO4•4H$_2$O" should read --MgSO$_4$•4H$_2$O--.

Column 6, line 27, "44I" should read --441--;
    line 51, "(A:" should be indented;
    line 53, "B:" should be indented;
    line 54, after "acid", insert --)--.

Column 7, line 66, "(23 2°C.)" should read --(23 ± 2°C)--.

Column 8, line 2, after "100%" (first occurrence), insert
-- ⎯⎯⎯> --.

Signed and Sealed this

Twelfth Day of July, 1994

Attest:

BRUCE LEHMAN

Attesting Officer      Commissioner of Patents and Trademarks